United States Patent [19]

Bode et al.

[11] 4,125,374
[45] Nov. 14, 1978

[54] METHOD AND APPARATUS FOR DETERMINING COMBUSTION MIXTURE AIR/FUEL RATIO

[75] Inventors: James D. Bode, Royal Oak; William G. Wolber, Southfield; Paul A. Michaels, Livonia; Charles J. Ahern, Lathrup Village, all of Mich.

[73] Assignee: Bendix Autolite Corporation, Fostoria, Ohio

[21] Appl. No.: 853,158

[22] Filed: Nov. 21, 1977

[51] Int. Cl.² .......................................... G01N 27/12
[52] U.S. Cl. ................................ 23/232 E; 73/27 R; 422/98
[58] Field of Search ............. 23/232 E, 254 E, 255 E; 73/27

[56] References Cited
U.S. PATENT DOCUMENTS

| | | | |
|---|---|---|---|
| 3,138,948 | 6/1964 | Pfefferle | 23/254 E |
| 3,149,921 | 9/1964 | Warner | 23/254 E X |
| 3,242,717 | 3/1966 | Matle et al. | 23/254 E X |
| 3,933,028 | 1/1976 | Laud et al. | 73/23 |
| 3,948,081 | 4/1976 | Wessel et al. | 73/23 |
| 4,025,412 | 5/1977 | Laconti | 204/195 R |

*Primary Examiner*—Robert M. Reese
*Attorney, Agent, or Firm*—William G. Kratz, Jr.; R. J. Eifler

[57] ABSTRACT

A wide range combustion mixture air/fuel ratio sensor in which an electrochemical cell supplies hydrogen gas to a palladium sensor element at a rate regulated by the output of a Wheatstone bridge circuit incorporating the sensor element. This generated hydrogen gas combines with any oxygen present in the exhaust gas through catalytic action and also maintains the level of absorbed hydrogen, and therefore the electrical resistance of the palladium sensor element, at a preselected value. The magnitude of the current applied to the electrochemical cell necessary to maintain this balance is a measure of the combustion mixture air/fuel ratio.

25 Claims, 8 Drawing Figures

METHOD AND APPARATUS FOR DETERMINING COMBUSTION MIXTURE AIR/FUEL RATIO

BACKGROUND OF THE INVENTION

1. Field of the Invention

This invention relates to a method and a sensor for determining the air/fuel ratio of a combustion mixture by measuring exhaust gas composition and more particularly to such a method and sensor which generate a signal proportional to the air/fuel ratio of such mixtures over a wide range of both rich and lean mixtures.

2. Prior Art

It has become desirable to determine the air/fuel ratio of combustion engine intake air/fuel mixtures to improve engine efficiency and reduce exhaust gas air pollution. Many combustion engine exhaust gas sensors in use today, such as the zirconium dioxide and titanium dioxide sensors which operate through thermal or deliberate catalytic action, or both, exhibit switch-like characteristics. That is: they generate one output for air/fuel mixtures rich of stoichiometry and another value lean of stoichiometry. Such sensors have drawbacks from a control system point of view since they do not allow the full mathematical processing abilities of the electronic control unit to be utilized. A two-state sensor that switches about the stoichiometric air/fuel ratio does not provide information for the employment of fuel enrichment techniques and lean zone operation. Moreover, a two-state sensor can be given only limited authority because such a control is inherently unstable and must oscillate. This application is limited to the three-way catalytic converter and duel bed emission control systems and is not extendable to the control of diesel or lean-burn control systems. Attempts to operate the zirconia and titania sensors over a range of oxygen partial pressures without catalysis, have encountered formidable difficulties, especially strong temperature sensitivity.

U.S. Pat. No. 3,933,028 discloses a sensor for detecting the air/fuel ratio of lean combustion engine intake mixtures. The partial pressure of oxygen present in the exhaust gas changes the electrical resistance of a cobalt monoxide ceramic sensor element. This change in resistance is used to generate an output signal which is a function of the partial pressure of oxygen in the lean regime. This device is only suitable, however, for generating signals representative of lean air/fuel ratios since the partial pressure of oxygen in combustion engine exhaust gases remains fairly constant for rich air/fuel intake mixtures.

U.S. Pat. No. 3,948,081 suggests that the steep slope of the signal in the area of stoichiometry produced by the prior art oxygen sensors can be smoothed out and a continuous signal representative of the air/fuel ratio can be generated by an electronic circuit which provides separate amplification factors for lean, rich and stoichiometric conditions. One difficulty with this approach is that, as mentioned above, the partial pressure of oxygen in combustion engine exhaust gases remains fairly constant for rich intake mixtures and hence is not a suitable parameter for determining the air/fuel ratio of such mixtures.

It is known that palladium has a high solubility for hydrogen and that the electrical resistance of a film of palladium will vary upon exposure to hydrogen by an amount corresponding to the hydrogen concentration. A hydrogen sensor operating on this principal is disclosed in the commonly owned U.S. Pat. No. 3,242,717. U.S. Pat. No. 3,138,948 discloses a hydrogen sensor in which a palladium containing resistance element generates an imbalance in a Wheatstone bridge circuit proportional to the partial pressure of hydrogen present in a test gas. A second resistance element covered with a hydrogen impervious coating provides temperature compensation for the bridge. Both of these sensors are used for the direct measurement of hydrogen partial pressures.

It is also known that hydrogen gas generators have been suggested for stabilizing electrochemical gas sensors. U.S. Pat. No. 4,025,412 discloses an electrochemical sensor in which the stabilizing hydrogen gas is generated within the sensor. A bias potential applied across the cell generates hydrogen ions at the sensing electrode from moisture in the test gas. The hydrogen ions are transported through the electrode to the reference electrode where they are reduced to molecular hydrogen and absorbed by an adjacent palladium foil. In this manner, an essentially constant partial pressure of internally generated hydrogen is maintained at the reference electrode. Catalytic action at the sensing electrode generates the sensor EMF while the hydrogen gas stabilizes the reference electrode potential at zero volts.

The primary object of the present invention is to provide an air/fuel mixture sensor which is continuously operative over a wide range of air/fuel mixtures from rich through lean, including stoichiometric. Yet another object is to provide such a sensor which is relatively insensitive to variations in temperature.

SUMMARY OF THE INVENTION

According to the invention, a wide range sensor for determining the air/fuel ratio of a combustion mixture from the hydrogen-oxygen content of the exhaust gases comprises a sensing element (19) exposed to the exhaust gases which reacts with hydrogen gas to change the electrical resistance of the sensing element (19) and which catalyzes reaction of oxygen and hydrogen. An electrochemical cell (1) generates hydrogen gas which is directed to the surface of the sensing element (19). Current for operation of the electrochemical cell (1) is generated by electric current generating means (35, 43, 49) as a function of the electrical resistance of the sensing element (19) This current is of a magnitude to generate hydrogen in the electrochemical cell (1) at a rate which maintains the electrical resistance of the sensing element (19) constant. An output device (51) generates a signal as a function of the current generated by the electric current generating means and therefore as a function of the hydrogen-oxygen content of the exhaust gases which in turn is a measure of the air/fuel ratio of the combustion mixture.

As applied to determining the intake air/fuel ratio for combustion engines, the invention takes advantage of the fact that the partial pressure of hydrogen in the exhaust gases increases with decreasing air/fuel ratios rich of stoichiometry where the oxygen partial pressure is low and fairly constant, and the fact that the oxygen partial pressure increases steadily lean of stoichiometry where the hydrogen partial pressure trails off to a trace amount. Thus for air/fuel ratios greater than stoichiometry, in the lean region, the electrochemical cell (1) generates sufficient hydrogen to combine with the oxygen and to maintain the electrical resistance of the sensing element at the preset value. For rich mixtures, below stoichiometry, virtually no hydrogen is needed to combine with oxygen in the exhaust gas and progressively more of the hydrogen needed to maintain the electrical resistance of the sensing element is provided by the rich mixture.

In the preferred embodiment of the invention, the electric current generating means includes a Wheatstone bridge (35) with the sensing element (19) connected in one leg of the bridge. The output of the bridge circuit drives the current source (49) connected to the electrochemical cell (1) which in turn generates the gas necessary to adjust the electrical resistance of the sensing element (19) in a manner which maintains the balance of the Wheatstone bridge circuit (35). A second sensing element (29) encapsulated in a gas impermeable, heat conductive material (31), or an electrical conductor with a temperature coefficient of resistivity similar to palladium but insensitive to hydrogen, and subject to the same heat conditions as the first sensing element (19) may be connected in the Wheatstone bridge circuit (35) to provide temperature compensation.

The electrochemical cell (1) may include a gas permeable hydrogen generating first electrode having a planar surface. A gas permeable electrical insulator (3) may be placed on this planar surface with the sensing element (19) affixed to the opposite side of the insulator (3). Preferably, the insulator (3) is a porous ceramic wafer and the sensing element (19) is a film of sensor material, preferably palladium, deposited on the wafer (3).

As an alternative to the Wheatstone bridge (35), the electric current generating means could include means (57) for generating a first signal proportional to the electrical resistance of the sensing element (19), and means (43) responsive to the first signal and a reference signal (SP) proportional to a preset value for the electrical resistance of the sensing element (19) to generate the control signal which in turn controls the current source (49) connected to the electrochemical cell (1).

Preferably, the sensing element (19) is a palladium film which may be overcoated with a material (27) such as platinum which passes hydrogen by diffusion to the palladium film (19) yet is less readily poisoned by unwanted gas species than palladium and is a better catalyst for the hydrogen-oxygen reaction. The palladium film (19) may also be provided with a gridded adherent undercoat (25) to provide a better bond to the gas permeable insulator without unduly restricting hydrogen diffusion.

As an additional feature of the invention, the electrolytic material (17) in the hydrogen generating electrochemical cell (1) may include a paste comprising an electrolyte, water and a reducing material which converts the oxygen gas generated along with the hydrogen to a solid-state by-product. To aid in the elimination of the oxygen gas generated by the electrochemical cell (1), the housing (7) which serves as the positive electrode may be made of zinc or may be zinc coated.

Alternative controlled sources of hydrogen gas could include electrical resistance heating elements to heat hydrides to release hydrogen gas or hydrogen gas chambers with electrical resistance devices to control the rate of escape of the hydrogen gas such as a palladium film window in the chamber.

It is also within the contemplation of the invention that the apparatus can be utilized generally to develop an output signal responsive to the hydrogen and/or oxygen content of a gaseous mixture. Furthermore, the invention is directed to a method of determining the hydrogen and/or oxygen content of a gaseous mixture comprising the steps of: exposing the gaseous mixture to one side of a two sided electrical resistor (19) whose resistance changes when exposed to hydrogen gas and which, if the presence of oxygen gas is to be determined, catalyzes the reaction of hydrogen and oxygen; generating hydrogen gas at a rate which is a function of an electrical current; exposing the other side of the resistor (19) to the hydrogen gas; measuring the resistance of the resistor (19); generating the electric current as a function of the resistance of the resistor (19); and providing an output signal which is a function of the current.

DESCRIPTION OF THE PREFERRED EMBODIMENTS

Figure 1:
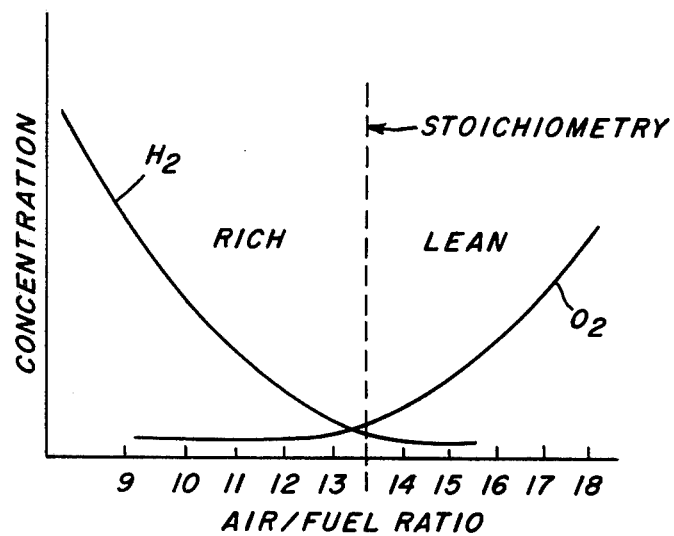
FIG. 1 is a graphic illustration of the oxygen and hydrogen gas concentrations in combustion engine exhaust gases for various air/fuel mixtures.

FIG. 1 illustrates the relative concentrations of oxygen and hydrogen present in combustion engine exhaust gases for rich through stoichiometric to lean conditions. This figure shows that the concentration or partial pressure of oxygen remains at a low, fairly constant value for rich air/fuel mixtures, but begins to rise as stoichiometric conditions are reached and then climbs steadily through the lean regime. On the other hand, FIG. 1 also shows that the concentration or partial pressure of hydrogen in combustion engine exhaust gases is high for low air/fuel mixtures, decreases steadily in value until stoichiometry is reached and then trails off to an insignificant amount in the lean region. The hydrogen concentration is therefore the best measure of the air/fuel ratio for rich combustion mixtures while the oxygen concentration provides a more accurate index for lean mixtures. The sensor now to be described in details takes advantage of these characteristics of combustion engine exhaust gases to provide an accurate, continuous measurement of the combustion mixture air/fuel ratio over a wide range of mixtures.

Figure 2:
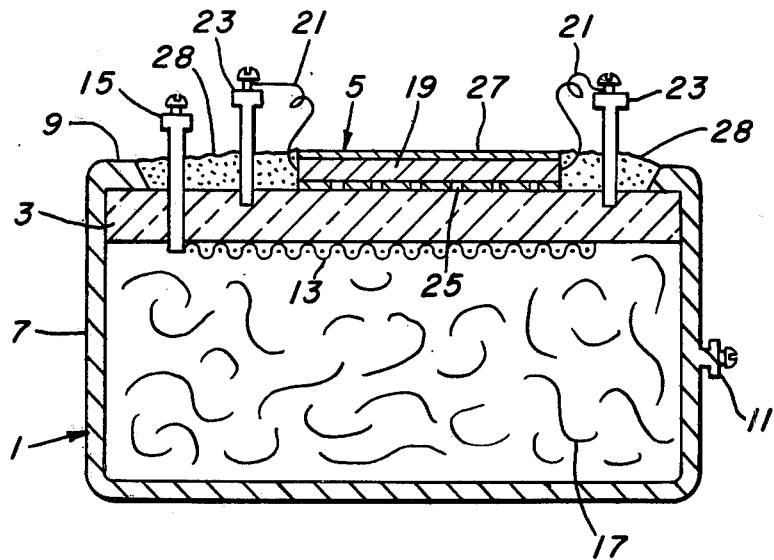
FIG. 2 is a sectional view through a sensor in accordance with the invention.

As shown in FIG. 2 a suitable sensor includes an electrochemical cell 1, a gas permeable insulator 3 and a sensing element 5 combined in an integral unit. The electrochemical cell includes a cup-shaped electrically conductive housing 7 provided with an annular, inwardly directed flange 9 at the open end. The housing 7 serves as one electrode of the electrochemical cell 1 and is provided with an electrical terminal 11. A grid-like second electrode 13, such as platinum gauze, is supported near the open end of the cup-shaped housing 7 by the gas permeable insulator 3 and is provided with an electric terminal 15.

The housing 7 is filled with electrolytic material 17. Semisolid electrolytes, such as aqueous pastes, gels or solution-impregnated plastics, felts or ion-exchange resins, are generally preferred over totally liquid electrolyte solutions. Water, acids, acid salts or hydrates can serve as the source of hydrogen in the electrolyte. Suitably, the electrolytic material 17 may comprise a paste of an electrolyte, water, a reducing material such as finely divided calcium, magnesium, zinc or aluminum and an inert material which serves as a thickener. As an example, the electrolyte can be calcium hydroxide, the inert material may be a small amount of calcium carbonate or diatomaceous earth, and the reducing material may be powdered zinc. Preferably, the housing 7 is made of zinc or is zinc coated. When an electric current is applied to the cell with terminal 11 positive and terminal 15 negative, gaseous hydrogen is formed at the platinum grid 13 and permeates through the gas permeable insulator 3. Any oxygen gas that forms along the interior of the housing 7 by electrolysis is eliminated by combination with the finely divided zinc and the zinc in the housing.

The gas permeable insulator 3 which supports the platinum gauze cathode 13 of the electrochemical cell is retained in the housing 7 by the annular flange 9. Suitable gas permeable insulators include ceramic wafers composed of materials such as porous alumina or zirconia or porous plastic sheets of polyethylene or polytetrafluroethylene or similar materials.

Deposited on the surface of the gas permeable insulator 3 opposite the electrochemical cell 1 and in the area inside the flange 9 on the housing 7, is the sensing element 5 comprising a film 19 of palladium, palladium-silver alloy, palladium-silver-rhodium alloy or any other material whose electrical conductivity is sensitive to hydrogen gas. Electrical leads 21 connected to the opposite ends of the palladium film 19 are secured to terminal posts 23 supported by the permeable insulator 3. The palladium film 19 may be provided with a gridded undercoat 25 such as gold or molybdenum to provide a better bond with the gas permeable insulator substrate without unduly restricting the diffusion of hydrogen. The palladium film 19 may also be overcoated with a material 27, such as platinum, which passes hydrogen by diffusion, is less readily poisoned by unwanted gas species than palladium and is a better catalyst for the hydrogen-oxygen reaction. A gas impervious sealer 28 assures that all of the hydrogen generated by the electrochemical cell 1 is directed to the palladium film 19 for efficient operation.

Figure 3:
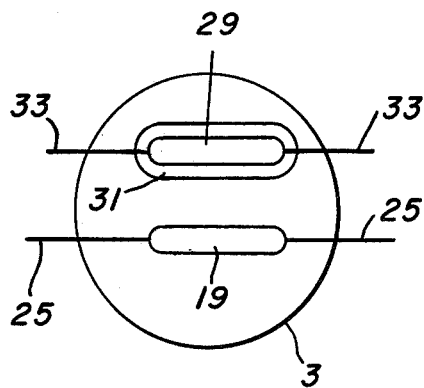
FIG. 3 is a plan view of a portion of the sensor of FIG. 2 showing the active and reference sensor elements.

As shown in FIG. 3, a temperature compensating element 29 is secured to the gas permeable insulator 3 adjacent the film 19. The compensating element 29 comprises a material that has a temperature coefficient of resistivity similar to that of the film 19 but which is unaffected by the presence of hydrogen or other exhaust gases. Platinum-gold, rhodium-gold or other noble metal alloys of selected composition may be utilized. However, in the embodiment of the invention disclosed, the compensating element 29 is a second film of palladium film encapsulated in a gas impermeable, electrically insulating, thermally conducting material 31 such as glass with electrical leads 33 connected to both ends of the film 29.

The palladium film 19 has a high solubility for hydrogen and its electrical resistance varies as a function of the concentration of absorbed hydrogen. The palladium film 19, and the platinum overcoat 27, if provided, also serve as catalysts for the oxidation of hydrogen. Hence, the concentration of absorbed hydrogen, and therefore the electrical resistance of the palladium film is related to the partial pressure of oxygen to which the strip is exposed. The glass encapsulated palladium or other compensating film 29 is unaffected by the hydrogen or oxygen present in the surrounding atmosphere; however, since it is exposed to the same physical operating conditions as the film 29, it may be used for temperature compensation in a manner discussed below.

Figure 4:
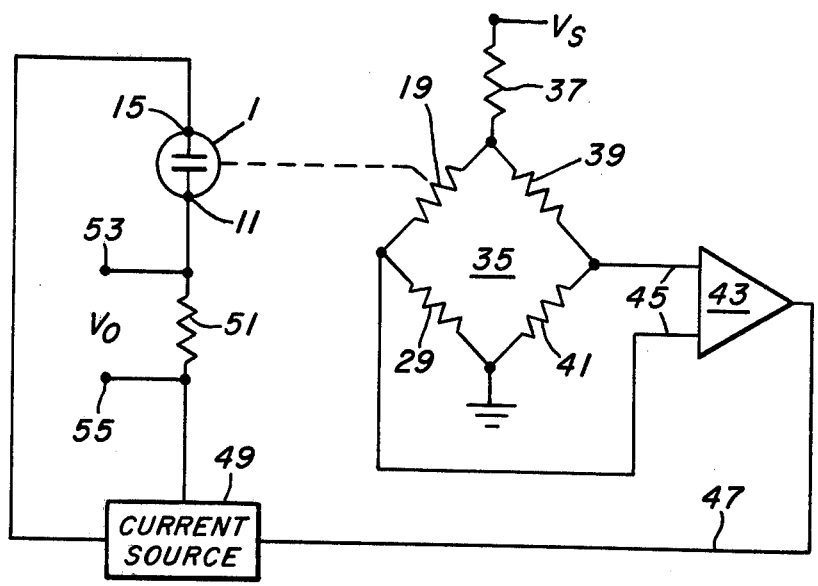
FIG. 4 is a schematic diagram illustrating a suitable electric current for the sensor according to the invention.

A suitable control circuit for the sensor is illustrated schematically in FIG. 4. The palladium and compensating films 19 and 29 are connected in adjacent legs of a grounded Wheatstone bridge circuit 35 which is energized by a voltage source Vs through resistor 37. Resistors 39 and 41 comprise the other two legs of the bridge circuit. The output of the bridge circuit 35 is applied to an operational amplifier 43 through electrical leads 45. The amplifier generates an output signal on lead 47 which is applied to a current source 49. The current source 49 supplies current to the electrochemical cell 1 through terminals 11 and 15 at a polarity and magnitude determined by the signal on the lead 47. A resistor 51 generates an output voltage across the terminals 53 and 55 proportional to the current supplied to the electrochemical cell 1. The cell in turn generates hydrogen gas which is applied to the palladium strip 19.

In operation, the housing 7 is mounted such that the palladium film 19 is exposed to the combustion engine exhaust gases. The amount of absorbed hydrogen in the palladium film 19, and therefore its electrical resistance, is dependent upon the concentrations of oxygen and/or hydrogen in the combustion gases as supplemented by the electrochemical cell 1 and as affected by the catalytic action of the palladium film and the platinum overcoat 27, if provided. The electrical resistance of the film 19 in turn affects the output of the Wheatstone bridge circuit 35 which is applied to the operational amplifier 43 through leads 45 to produce a control signal on lead 47. This control signal regulates the current applied by the current source 49 to the electrochemical cell 1 through terminals 11 and 15 and therefore regulates the rate at which hydrogen and oxygen are generated by the cell. The gas generated at the electrode 13 of cell 1 permeates through the porous insulator 3 to the palladium film 19 to complete the control loop. The parameters of the loop are such that sufficient gas is generated to maintain the electrical resistance of the palladium film 19 at a preselected value over a wide range of combustion gas hydrogen-oxygen partial pressures. The glass encapsulated palladium film or other compensating film 29 which is exposed to the same temperature of the exhaust gases as film 19 but is not subjected to the direct contact of these gases, provides temperature compensation in the bridge circuit.

In the lean region where the partial pressure of oxygen in the exhaust gases is significant while the partial pressure of hydrogen is very low, hydrogen gas is generated at the electrode 13 at a sufficient rate to combine with the oxygen which comes in contact with the palladium film 19 and to maintain the level of absorbed hydrogen in the palladium film at the level necessary to maintain the preselected electrical resistance. As stoichiometry is approached, less hydrogen is needed to combine with the oxygen and as the mixture becomes rich, less supplemental hydrogen is required to maintain the preselected electrical resistance of the palladium film 19. Depending upon the balance point selected for the Wheatstone bridge circuit, the parameters can be selected such that hydrogen is always formed at electrode 13 of cell 1 but at a decreasing rate for very rich mixtures.

Figure 5:
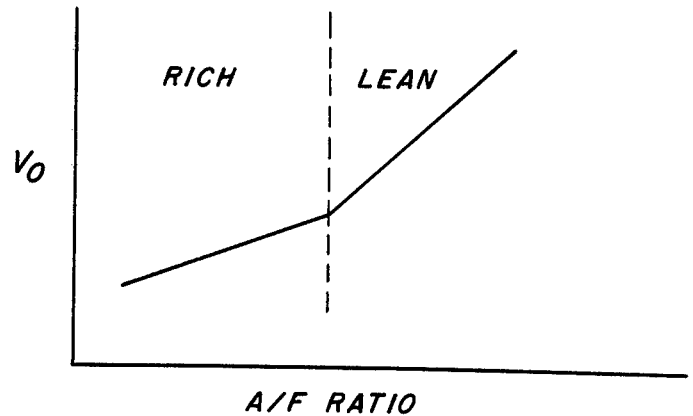
FIG. 5 is a graphic illustration of the response of the circuit of FIG. 4.

FIG. 5 illustrates the relationship of the sensor output voltage Vo appearing across the terminals 53 and 55 to the air/fuel ratio. It can be seen that the slope of this function is steeper in the lean than in the rich region. This is due to the fact that the oxygen concentration in the exhaust gases increases substantially in the lean region and that two hydrogen molecules are required to combine with each oxygen molecule in the reaction taking place at the palladium film or at the platinum overcoat, if provided.

Figure 6:
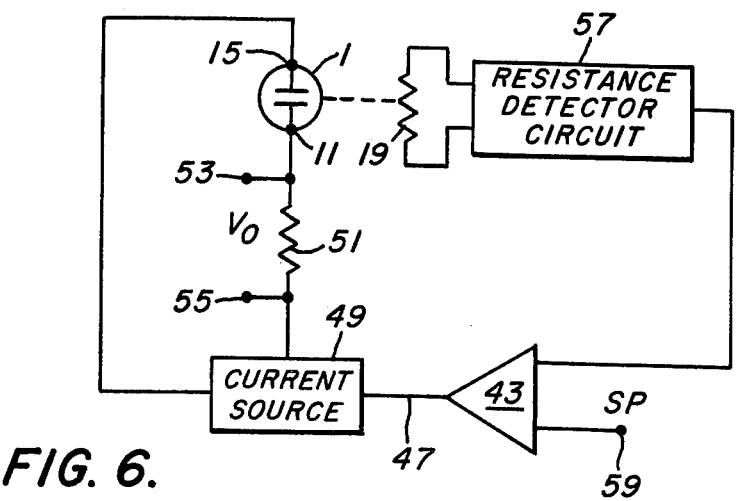
FIG. 6 is a schematic diagram of another electric circuit suitable for the sensor in accordance with the invention.

As an alternate to the Wheatstone bridge circuit 35 utilized in the circuit of FIG. 4, a resistance detector circuit 57 could be used in its place, as shown in FIG. 6. In this instance, a set point signal SP would have to be applied to the second input 59 of the operational amplifier 43. In all other respects the control system would operate the same as that shown in FIG. 4. The bridge circuit 35 in FIG. 4 may also be replaced by a full bridge using two active palladium films and two temperature compensating strips. As in the circuit of FIG. 6, a set point input would be required.

Figure 7:
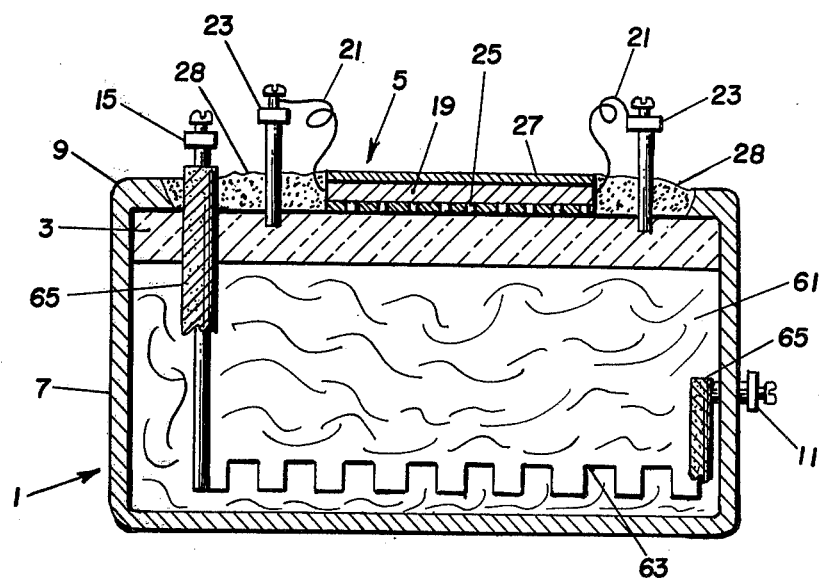
FIG. 7 is a sectional view through another embodiment of a sensor in accordance with the invention.

Alternate controlled sources of hydrogen gas can also be used in place of the electrochemical cell. For instance, hydrides which may be heated by an electrical resistance heating element to generate hydrogen gas could provide a safe solidstate source of hydrogen. As illustrated in FIG. 7, a packed bed of a solid metal hydride 61 is provided in the housing 7. Such well known hydrides include solid metal hydrides such as vanadium hydride, magnesium hydride, magnesium-nickel hydride, iron-titanium hydride and the like, which store large amounts of hydrogen which is liberated when the hydride is heated. The rate of hydrogen evaluation from the hydride, as is known, increases as the temperature is increased. A heating element 63 provides the thermal energy to heat the hydride. The amount of electrical current supplied to the heating element 63, by way of the electrical contacts 11 and 15, controls the temperature of the hydride. This current is then a measure of the amount of hydrogen needed to restore the resistance of sensing element 19 to the balanced condition. The heating element and its connecting leads can be insulated with a ceramic coating 65 or sleeves as is commonly done with heating units. A chamber of hydrogen gas with a palladium film window which would control the release of hydrogen as a function of an electric current applied across the palladium would provide another alternative hydrogen source.

Figure 8:
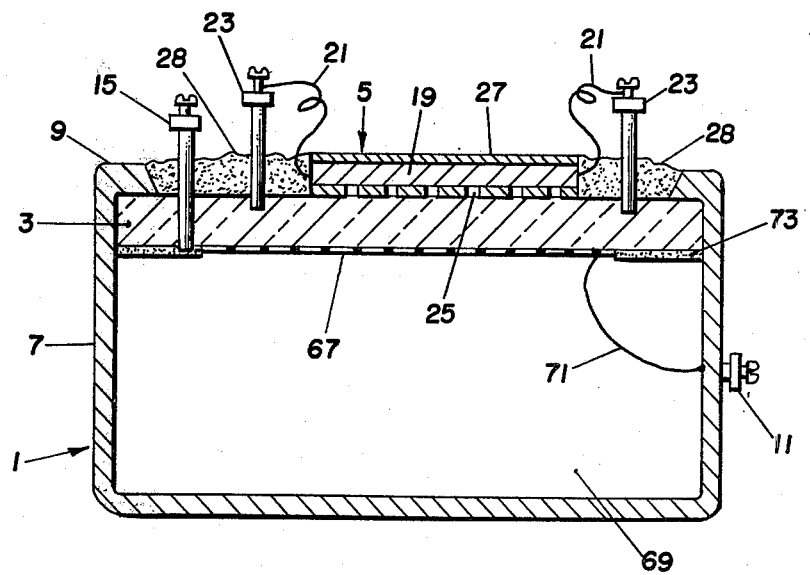
FIG. 8 is a sectional view through a further embodiment of a sensor in accordance with the invention.

As illustrated in FIG. 8, a thin palladium film window 67 acts as an electrically controlled proportioning valve for hydrogen gas contained in reservoir 69 formed by the housing 7. When electric current is applied to the palladium window through contacts 11 and 15 and connecting lead 71, the palladium becomes warm and permits hydrogen gas to diffuse therethrough. The hydrogen can then pass through the porous wafer 3 to reach the sensing element 19. The rate of hydrogen diffusion depends on the amount of current applied. The current therefore is a measure of the amount of hydrogen needed to restore the balancing resistance in sensing element 19. A glaze seal 73 may be provided to prevent hydrogen gas from reaching the wafer except through the palladium window 67.

The air/fuel ratio sensor of this invention provides a continuous output signal proportional to the air/fuel ratio over a wide range. As such, it is suitable for use with lean burn and fuel enrichment control techniques as well as diesel control systems. It should also be appreciated that the sensor can measure oxygen concentration alone in the event that the measured gases contain only oxygen plus other gases without any hydrogen. There are a number of applications for which an instrument of this type is desirable, besides that of an engine which is always operated lean. For example, in certain industrial processes oxygen concentration may be a sensitive control parameter. An example would be in the processing of iron to make steel. Certain types of hazardous operations require oxygen measuring instrumentation, such as diving underwater, crewing high performance aircraft, and underground mining. Oxygen measuring instruments are also used medically in the treatment of respiratory patients and in surgical procedures. Finally, the utility of oxygen and/or hydrogen measurement is not confined to engine control, but can also be applied to combustion control in general, as in the case of fossil-fueled power plants; such instrumentation can also be applied to processes for coal gasification, such as the reaction of coal, air and water to form the mixture of hydrogen and carbon monoxide commonly known as producer gas.

These examples above are cited so as to indicate that this invention has general utility as an instrument for measuring oxygen or hydrogen alone or with other gases, and also in combination and with other gases, in the general sense; and that the invention is not limited in its application to the control of engines by means of measuring their exhaust gases. While specific embodiments of the invention have been disclosed in detail, the invention is not to be limited by such descriptions but it is to be given the full scope and range of the appended claims.

We claim:

1. A wide range sensor for determining the air/fuel ratio of a combustion mixture from the gaseous hydrogen and oxygen content of the exhaust gases comprising:

a sensing element which reacts with hydrogen gas to change the electrical resistance of said sensing element and which catalyzes the reaction of hydrogen gas with oxygen gas, said sensing element being exposed to said exhaust gases;

an electrochemical cell which generates hydrogen gas at a rate which is a function of the magnitude of an electric current applied to said cell;

means for directing the hydrogen gas generated by the electrochemical cell to the surface of the sensing element;

means for generating an electric current as a function of the electrical resistance of the sensing element which current, when applied to the electrochemical cell, is of a magnitude to generate hydrogen gas at a rate which maintains the electrical resistance of said sensing element constant; and output means generating an output signal as a function of the current applied to the electrochemical cell, whereby said output signal is proportional to the gaseous hydrogen and oxygen content of the exhaust gases and therefore air/fuel ratio of said combustion mixture.

2. The sensor of claim 1 wherein the electric current generating means includes means for generating a first signal as a function of the electrical resistance of said sensing element, a current source for generating said current which is applied to the electrochemical cell, and means responsive to the first signal and a reference signal which is proportional to a preset value for the electrical resistance of said sensing element to generate a control signal which controls the current generated by the current source to maintain the electrical resistance of said sensing element at said preset value.

3. The sensor of claim 1 in which the sensing element has an adherent gridded undercoat.

4. The sensor of claim 1 in which the electrolytic material in the hydrogen generating electrochemical cell includes a paste comprising an electrolyte, water and a reducing agent.

5. The sensor of claim 1 in which the positive electrode of the electrochemical cell contains zinc.

6. The sensor of claim 1 in which the positive electrode of the electrochemical cell is coated with zinc.

7. The sensor of claim 1 in which the sensing element is a palladium film.

8. The sensor of claim 7 in which the palladium film is overcoated with platinum.

9. The sensor of claim 1 wherein said electric current generating means includes a Wheatstone bridge circuit with said sensing element connected in a first leg thereof, a current source connected in series with said electrochemical cell and means connected across the bridge circuit for controlling the current applied by the current source to the electrochemical cell to generate hydrogen gas at a rate to adjust the electrical resistance of the sensing element and maintain the Wheatstone bridge in balance.

10. The sensor of claim 9 including a temperature compensating element having an electrical resistance with a temperature coefficient similar to that of the sensing element but which is unaffected by the presence of hydrogen and the other exhaust gases mounted adjacent the sensing element and therefore subject to substantially the same thermal conditions as said sensing element, said temperature compensating element being electrically connected in a second leg of the Wheatstone bridge circuit to provide temperature compensation therefor.

11. The sensor of claim 10 wherein said temperature compensating element comprises the same material as the sensing element encapsulated in a gas impermeable, heat conductive material.

12. The sensor of claim 1 wherein said electrochemical cell includes a gas permeable, hydrogen generating first electrode having a planar surface and including a gas permeable electrical insulator having a first surface confronting said gas permeable planar surface of said first electrode with said sensing element affixed to a second parallel surface of said insulator.

13. The sensor of claim 12 wherein said insulator is a porous ceramic wafer and said sensing element is a film of sensor material deposited on said second surface of said ceramic wafer.

14. The sensor of claim 13 including a second sensing element encapsulated in a gas impermeable, heat conductive material deposited on said second surface of said ceramic wafer adjacent the first sensing element such that both sensing elements are subjected to substantially the same thermal conditions, said second sensing element being connected in said control means to provide thermal compensation thereto.

15. An apparatus responsive to the hydrogen content in a gaseous mixture, comprising:
means for generating hydrogen gas at a rate which is a function of an applied electric current;
an electrical resistor whose resistance changes when exposed to a gas containing hydrogen, said resistor having two sides, one of which is exposed to said gaseous mixture and the other exposed to the hydrogen generated by said hydrogen gas generating means;
means for supplying an electrical current to said hydrogen gas generating means, said current varying as a function of the electrical resistance of said resistor; and
means for providing an output signal which is a function of said variable electrical current.

16. The apparatus of claim 15 wherein said electrical resistor catalyzes the reaction of hydrogen and oxygen, whereby said output signal is a function of the hydrogen-oxygen content of said gaseous mixture.

17. The apparatus of claim 15 wherein said variable electrical current decreases as the electrical resistance of the resistor increases, to reduce the amount of hydrogen gas generated by the hydrogen gas generating means.

18. The apparatus of claim 15 wherein said hydrogen generating means comprises an electrochemical cell.

19. The apparatus of claim 15 wherein said hydrogen generating means comprises a hydride and a resistance heating element responsive to said electric current to heat said hydrides to generate hydrogen as a function of the electric current.

20. The apparatus of claim 15 wherein said hydrogen generating means comprises a chamber containing hydrogen gas and a palladium film window in said chamber across which said electric current is applied to control the rate at which hydrogen gas escapes from said chamber through said palladium window.

21. A method of determining the hydrogen content of a gaseous mixture comprising:
exposing said gaseous mixture to one side of a two sided electrical resistor whose resistance changes when exposed to hydrogen gas;
generating hydrogen gas at a rate which is a function of the magnitude of an electrical current;
exposing the other side of said resistor to said hydrogen gas;
measuring the resistance of said resistor;
generating said electrical current as a function of the resistance of said resistor; and
providing an output signal which is a function of said electric current.

22. The method of claim 21 wherein said electrical resistor catalyzes the reaction of hydrogen and oxygen whereby said output signal is a function of the hydrogen-oxygen content of said gaseous mixture.

23. The method of claim 21 wherein the generated electric current decreases as the resistance of the resistor increases.

24. Apparatus responsive to the oxygen content in a gaseous mixture, comprising:
means for generating hydrogen gas at a rate which is a function of an applied electric current;
an electrical resistor whose resistance changes when exposed to a gas containing hydrogen and which catalyzes the reaction of oxygen and hydrogen, said resistor having two sides, one of which is exposed to said gaseous mixture and the other exposed to the hydrogen generated by said hydrogen gas generating means;

means for supplying an electrical current to said hydrogen gas generating means, said current varying as a function of the electrical resistance of said resistor; and means for providing an output signal which is a function of said variable electrical current.

25. A method of determining the oxygen content of a gaseous mixture comprising:

exposing said gaseous mixture to one side of a two sided electrical resistor whose resistance changes when exposed to hydrogen gas and which catalyzes the reaction of hydrogen and oxygen;

generating hydrogen gas at a rate which is a function of the magnitude of an electrical current;

exposing the other side of said resistor to said hydrogen gas;

measuring the resistance of said resistor;

generating said electrical current as a function of the resistance of said resistor; and providing an output signal which is a function of said electric current.

* * * * *